(12) United States Patent
Ma

(10) Patent No.: US 11,654,240 B2
(45) Date of Patent: May 23, 2023

(54) LOW DOSE SYRINGE INCLUDING AN AIR VENTING SYSTEM

(71) Applicant: Becton, Dickinson and Company, Franklin Lakes, NJ (US)

(72) Inventor: Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 140 days.

(21) Appl. No.: 16/413,905

(22) Filed: May 16, 2019

(65) Prior Publication Data

US 2019/0366004 A1 Dec. 5, 2019

Related U.S. Application Data

(60) Provisional application No. 62/679,153, filed on Jun. 1, 2018.

(51) Int. Cl.
*A61M 5/178* (2006.01)
*A61M 5/315* (2006.01)
(Continued)

(52) U.S. Cl.
CPC ...... *A61M 5/31513* (2013.01); *A61M 5/1782* (2013.01); *A61M 5/36* (2013.01);
(Continued)

(58) Field of Classification Search
CPC .. A61M 5/3135; A61M 5/178; A61M 5/1782; A61M 2005/3123; A61M 5/31513; A61M 5/31511; A61M 5/36
See application file for complete search history.

(56) References Cited

U.S. PATENT DOCUMENTS 4,795,444 A * 1/1989 Hasegawa ............... A61M 3/00
604/218
5,238,003 A 8/1993 Baidwan et al.
(Continued)

FOREIGN PATENT DOCUMENTS

CN 203898851 U 10/2014
EP 2366418 A2 9/2011
(Continued)

OTHER PUBLICATIONS

PCT international Search Report and Written Opinion in PCT/US2019/032790 dated Aug. 2, 2019, 13 pages.

*Primary Examiner* — Bhisma Mehta
*Assistant Examiner* — William R Frehe
(74) *Attorney, Agent, or Firm* — Servilla Whitney LLC

(57) ABSTRACT

Medical devices capable of filling liquid into a syringe barrel while evacuating any air from the syringe are described. An exemplary medical device includes a syringe barrel having a tapered sidewall portion for permitting air to vent from the chamber and preventing liquid from exiting the chamber, a plunger rod, and stopper. Another exemplary medical device includes a syringe barrel having a plurality of air venting grooves associated with the sidewall of the barrel, a plunger rod and stopper. Also described is a medical device including a syringe barrel, plunger rod and stopper having a porous plug. Described is a medical device including a syringe barrel having a plurality of air venting grooves associated with the sidewall of the barrel and a porous membrane disposed over the air venting grooves, a plunger rod and stopper. Methods for filling a syringe barrel with a liquid are also provided.

16 Claims, 8 Drawing Sheets

(51) Int. Cl.
*A61M 5/36* (2006.01)
*A61M 5/31* (2006.01)

(52) U.S. Cl.
CPC ............ *A61M 2005/3123* (2013.01); *A61M 2205/3379* (2013.01); *A61M 2207/00* (2013.01); *A61M 2209/045* (2013.01)

(56) References Cited

U.S. PATENT DOCUMENTS

| | | | |
|---|---|---|---|
| 5,779,668 A * | 7/1998 | Grabenkort | A61M 5/3129 604/218 |
| 2008/0171994 A1* | 7/2008 | Williams | A61M 5/3135 604/187 |
| 2011/0092903 A1 | 4/2011 | Caizza et al. | |
| 2014/0039462 A1* | 2/2014 | Ingram | A61J 15/0096 604/125 |
| 2014/0188052 A1* | 7/2014 | Kawamura | A61M 5/315 604/220 |
| 2018/0304012 A1* | 10/2018 | Jansen | B65B 7/2821 |
| 2019/0009035 A1* | 1/2019 | Lum | A61B 5/150213 |
| 2019/0054240 A1* | 2/2019 | Takeuchi | A61M 5/31 |

FOREIGN PATENT DOCUMENTS

| | | |
|---|---|---|
| WO | 96/30066 A1 | 10/1996 |
| WO | 03/028785 A2 | 4/2003 |

* cited by examiner

LOW DOSE SYRINGE INCLUDING AN AIR VENTING SYSTEM

CROSS-REFERENCE TO RELATED APPLICATIONS

This application claims priority under 35 U.S.C. § 119(e) to U.S. Provisional Application No. 62/679,156, filed Jun. 1, 2018, the disclosures of which are incorporated herein by reference in their entireties.

TECHNICAL FIELD

Aspects of the present disclosure relate to medical devices capable of evacuating air trapped within the medical device while filling the medical device with liquid.

BACKGROUND

Syringe barrels contain, store, transfer and measure liquids, typically containing medicaments or other fluids for delivery to a patient. Medical devices, including plunger rods and stoppers, are used to aspirate and expel liquid from syringe barrels. During aspiration, air can become trapped within the syringe barrel. The presence of air within the syringe barrel can result in inaccurate dosage measurements and other issues.

Typically, air is removed from syringe barrels, by inverting the syringe barrel to force the air trapped within the barrel to the opening through which the fluid is aspirated. The air is then expelled through the opening by applying a force on the plunger rod in the distal direction. This expulsion process, however, can result in the expulsion of a portion of the liquid aspirated into the syringe barrel. In addition, this method of removing air from the syringe barrel may require the user to agitate the barrel of the syringe to force the air bubbles to move toward the opening.

There is a need to provide a device to facilitate the removal of air trapped in the barrel during dose preparation to reduce preparation time and improve clinician efficiency.

SUMMARY

Several aspects of a medical device including structure to evacuate air from a syringe barrel when filling liquid into the syringe barrel are provided. Exemplary syringe barrels described herein include a side wall having an interior surface defining a chamber for retaining fluid, an open proximal end and a distal end including a distal wall with a tip extending distally therefrom having an open passageway in fluid communication with said chamber. The medical devices include a plunger rod and stopper disposed within the chamber of the syringe barrels or other containers.

A first aspect of the present disclosure pertains to a medical device including a syringe barrel having an open proximal end, a distal end and a distal wall. A sidewall extends from the distal end to the open proximal end and includes an interior surface that defines a chamber for retaining or holding fluids, which may include liquid medication and/or other liquids. A tip extending distally from the distal wall. The tip having an open passageway there through in fluid communication with the chamber.

The medical device also includes a plunger rod having a proximal end, a distal end and a body extending from the proximal end to the distal end. The plunger rod is disposed within the chamber and moveable in the proximal and distal direction within the chamber.

The medical device also includes a stopper having a distal face and a proximal end. The stopper is attached to the plunger rod. The stopper is disposed within the chamber and moveable in the proximal and distal direction within the chamber.

Sidewall of the syringe barrel includes a first sidewall portion and a second sidewall portion. First sidewall portion is disposed at the distal end of the barrel. First sidewall portion has an inner diameter equal to or smaller than an outer diameter of the stopper to form a releasable fluid-tight seal between the stopper and the interior surface of the sidewall of the barrel. Second sidewall portion is disposed at the open proximal end of the barrel. Second sidewall portion includes a taper. Second sidewall portion has an inner diameter larger than the outer diameter of the stopper forming a gap between the interior surface of the sidewall and stopper causing the releasable seal between the stopper and the sidewall of the barrel to break thereby permitting air to vent from the chamber while preventing liquid from exiting the chamber. In one or more embodiments, the inner diameter of the second sidewall portion increases gradually in the proximal direction.

In one or more embodiments, the distal end of the plunger rod is disposed within the barrel and the stopper forms a releasable seal with the sidewall of the barrel having an inner diameter equal to or smaller than the outer diameter of the stopper. The releasable fluid-tight seal between the stopper and the interior surface of the sidewall of the barrel is broken when the stopper reaches the taper of the second sidewall portion at the open proximal end of the barrel.

In one or more embodiments, upon movement of the plunger rod in a distal direction relative to the taper of the second sidewall portion at the open proximal end of the barrel, the releasable seal is re-formed allowing the fluid within the chamber to be expelled through the open passageway of the tip in fluid communication with said chamber.

In one or more embodiments, medical device includes a barrel graduation line. In one or more embodiments, the second sidewall portion is proximal to the barrel graduation line.

Another aspect of the present disclosure pertains to a method for filling a syringe barrel with a liquid including providing a medical device of the as described herein. The tip of the syringe barrel is submerged in a liquid and an air source and the liquid is drawn into the chamber prior to reaching the tapered sidewall of the barrel. The air source is evacuated from the chamber by moving the plunger rod in a proximal direction past the second sidewall portion of the barrel to allow the stopper to break the releasable fluid-tight seal between the stopper and the interior surface of the sidewall of the barrel when the stopper reaches the gap formed by the second sidewall portion for permitting air to vent from the chamber and preventing liquid from exiting the chamber. The releasable fluid-tight seal is re-formed upon contact of the stopper with the first sidewall portion allowing the fluid within the chamber to be expelled through the open passageway of the tip in fluid communication with said chamber.

Another aspect of the present disclosure pertains to a medical device including a syringe barrel including a sidewall having an interior surface defining a chamber for retaining a liquid, an open proximal end, a distal end including a distal wall with a tip extending distally therefrom having an open passageway in fluid communication with said chamber. The sidewall includes a first sidewall portion and a second sidewall portion. The medical device includes a plunger rod having a proximal end, a distal end and a body extending from the proximal end to the distal end. The plunger rod is disposed within the chamber and is moveable in the proximal and distal direction within the chamber. The medical device includes a stopper disposed within the chamber. The stopper includes a distal face and a proximal end. The stopper is moveable in the proximal and distal direction within the chamber. The distal end of the barrel includes the first sidewall portion to form a releasable fluid-tight seal between the stopper and the interior surface of the first sidewall portion of the barrel. In one or more embodiments, the open proximal end of the barrel includes the second sidewall portion having one air venting groove embedded within the second sidewall portion of the barrel to break the releasable seal between the stopper and the sidewall of the barrel for permitting air to vent from the chamber and preventing liquid from exiting the chamber. In one or more embodiments, the open proximal end of the barrel includes the second sidewall portion including a plurality of air venting grooves embedded within the second sidewall portion of the barrel to break the releasable seal between the stopper and the sidewall of the barrel for permitting air to vent from the chamber and preventing liquid from exiting the chamber.

The stopper forms a releasable fluid-tight seal with the first sidewall portion of the barrel when the distal end of the plunger rod is disposed within the first sidewall portion.

The stopper breaks the releasable fluid-tight seal between the stopper and the first sidewall portion of the barrel when the distal end of the plunger rod is disposed within the second sidewall portion.

Upon movement of the plunger rod in a distal direction from the second sidewall portion towards the first sidewall portion, the releasable fluid-tight seal is re-formed upon contact of the stopper with the first sidewall portion allowing the fluid within the chamber to be expelled through the open passageway of the tip in fluid communication with said chamber.

Another aspect of the present disclosure pertains to a method for filling a syringe barrel with liquid, including providing a medical device as described herein. The tip of the syringe barrel is submerged in a liquid and an air source and the liquid are drawn into the chamber prior to reaching the plurality of air venting grooves embedded within the second sidewall portion of the barrel. The air source is evacuated from the chamber by moving the plunger rod in a proximal direction past the plurality of air venting grooves embedded within the second sidewall portion of the barrel to allow the stopper to break the releasable fluid-tight seal between the stopper and the interior surface of the first sidewall portion of the barrel for permitting air to vent from the chamber and preventing liquid from exiting the chamber. The releasable fluid-tight seal is re-formed upon contact of the stopper with the first sidewall portion allowing the fluid within the chamber to be expelled through the open passageway of the tip in fluid communication with said chamber.

Another aspect of the present disclosure pertains to a medical device including a syringe barrel having a sidewall having an interior surface defining a chamber for retaining a liquid, an open proximal end and a distal end including a distal wall with a tip extending distally therefrom having an open passageway in fluid communication with said chamber. The sidewall having a first side-wall portion and a second side-wall portion. A plunger rod including a proximal end, a distal end and a body extending from the proximal end to the distal end. The plunger rod disposed within the chamber and moveable in the proximal and distal direction within the chamber. A stopper disposed within the chamber and moveable in the proximal and distal direction within the chamber, the stopper having a stopper including a distal face, a proximal end.

The distal end of the barrel includes the first sidewall portion to form a releasable fluid-tight seal between the stopper and the interior surface of the first sidewall portion of the barrel. The open proximal end of the barrel includes the second sidewall portion including a plurality of air venting grooves embedded within the interior surface of the second sidewall portion of the barrel to break the releasable seal between the stopper and the sidewall of the barrel.

A porous membrane is disposed over the plurality of air venting grooves to permit air to flow out of the chamber and to prevent liquid from exiting the chamber.

In one or more embodiments, the stopper forms a releasable fluid-tight seal with the first sidewall portion of the barrel when the distal end of the plunger rod is disposed within the first sidewall portion. The stopper breaks the releasable fluid-tight seal between the stopper and the first sidewall portion of the barrel when the distal end of the plunger rod is moved over the porous membrane disposed over the plurality of air venting grooves of the second sidewall portion. Upon movement of the plunger rod in a distal direction from the second sidewall portion towards the first sidewall portion, the releasable fluid-tight seal is re-formed upon contact of the stopper with the first sidewall portion allowing the fluid within the chamber to be expelled through the open passageway of the tip in fluid communication with said chamber.

In one or more embodiments, the porous membrane disposed over the plurality of air venting grooves extends in a direction substantially parallel to a longitudinal axis of the chamber. In one or more embodiments, the porous membrane disposed over the plurality of air venting grooves is disposed along a portion of the second sidewall portion. In one or more embodiments, the porous membrane disposed over the plurality of air venting grooves is disposed along an entire length of the second sidewall portion.

Another aspect of the present disclosure pertains to a method for filling a syringe barrel with liquid, including providing a medical device of the as described herein and submerging the tip of the syringe barrel in a liquid. An air source and the liquid are drawn into the chamber prior to reaching the one air venting groove or the plurality of air venting grooves embedded within the second sidewall portion of the barrel. The air source is evacuated from the chamber by moving the plunger rod in a proximal direction past the porous membrane disposed over the plurality of air venting grooves embedded within the second sidewall portion of the barrel to allow the stopper to break the releasable fluid-tight seal between the stopper and the interior surface of the first sidewall portion of the barrel for permitting air to vent from the chamber and preventing liquid from exiting the chamber. The releasable fluid-tight seal is re-formed upon contact of the stopper with the first sidewall portion allowing the fluid within the chamber to be expelled through the open passageway of the tip in fluid communication with said chamber.

Another aspect of the present disclosure pertains to a medical device including a syringe barrel having a side wall with an interior surface defining a chamber for retaining fluid, an open proximal end and a distal end including a distal wall with a tip extending distally therefrom having an open passageway in fluid communication with said chamber. The medical device includes a plunger rod having a proximal end, a distal end and a body extending from the proximal end to the distal end. The plunger rod is disposed within the chamber and moveable in the proximal and distal direction within the chamber. The medical device also includes a stopper disposed within the chamber and moveable in the proximal and distal direction within the chamber. The stopper forms a fluid-tight seal with the interior surface of the syringe barrel. The stopper includes a distal face having an opening, a proximal end, and a channel extending from the distal face to the proximal end. A porous plug is disposed within the channel of the stopper to permit air to flow from the chamber and to prevent liquid from exiting the chamber.

In one or more embodiments, the porous plug includes a selective barrier that defines a liquid penetration pressure and an air penetration pressure that is less than the liquid penetration pressure. In one or more embodiments, the selective barrier includes one of a hydrophobic filter, a swellable polymer or a combination thereof.

In one or more embodiments, the plunger rod includes a channel disposed in body of the plunger rod extending from the proximal end of the plunger rod to the distal end of the plunger rod. The channel of the plunger rod is in fluid communication with the channel of the stopper.

In one or more embodiments, the medical device includes a removable plunger cap inserted in the channel at the proximal end of plunger rod.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways. It is to be understood that the configurations shown in FIGS. 1-13 are merely exemplary, and the components can be different in shape and size than shown.

With respect to terms used in this disclosure, the following definitions are provided.

In this disclosure, a convention is followed wherein the distal end of the device is the end closest to a patient and the proximal end of the device is the end away from the patient and closest to a practitioner.

As used herein, the use of "a," "an," and "the" includes the singular and plural.

As used herein, the use of "plurality" includes the singular and plural.

The embodiments of the present disclosure described herein, with specific reference to various aspects, provides for a medical device including syringe barrel or other containers to draw liquid from a source into the syringe barrel. Because a syringe has a nozzle where the plunger stopper does not contact, some air will be drawn into the syringe barrel when fluid, such as medication, is drawn in preparation for injection. The air will be trapped between the fluid and the stopper. The trapped air needs to be purged from the syringe to set up the proper injection volume. However, it is very difficult to purge the trapped air from the syringe, particularly for low dose syringe such as the 1 ml oral, enteral, and/or hypodermic syringe. The present disclosure pertains to a low dose syringe with means to vent the air trapped in the barrel during dose preparation. The medical devices described herein generally include a plunger rod and stopper that allow the removal or evacuation of air from the liquid drawn into the syringe barrel or other container. The embodiments of the medical device may be used with other types of containers, in addition to syringe barrels, for example, needleless IV sets or other devices having a chamber that can be used to store and/or transfer liquid medication and/and/or other liquids. Syringe barrels described herein may include optional needle hubs, integrated needle cannulas and/or needle shields.

Figure 1:
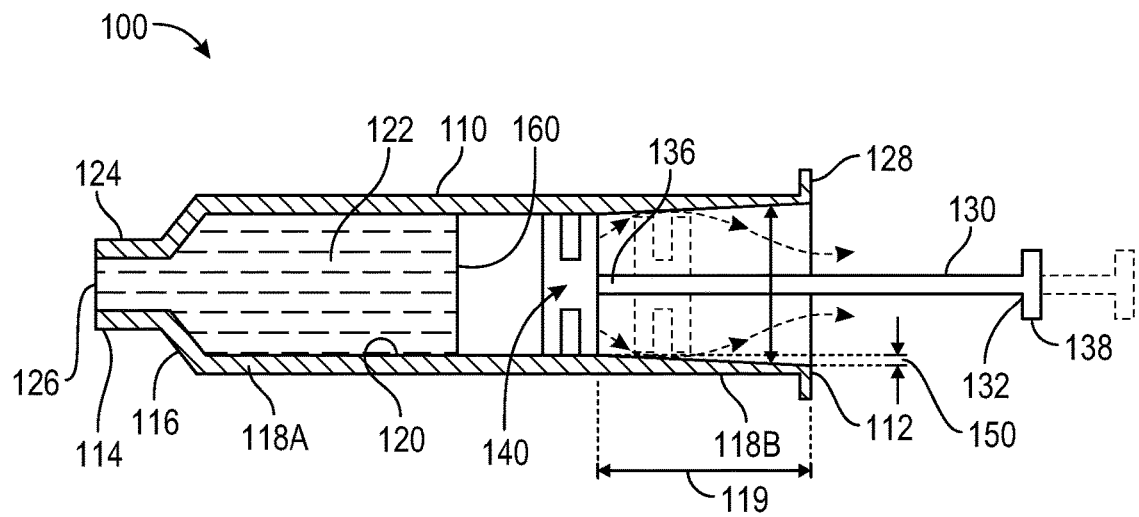
FIG. 1 shows a cross-sectional side view of a medical device having a barrel with a tapered sidewall, the device including a plunger rod and stopper according to a first aspect of the present disclosure.
Figure 2:
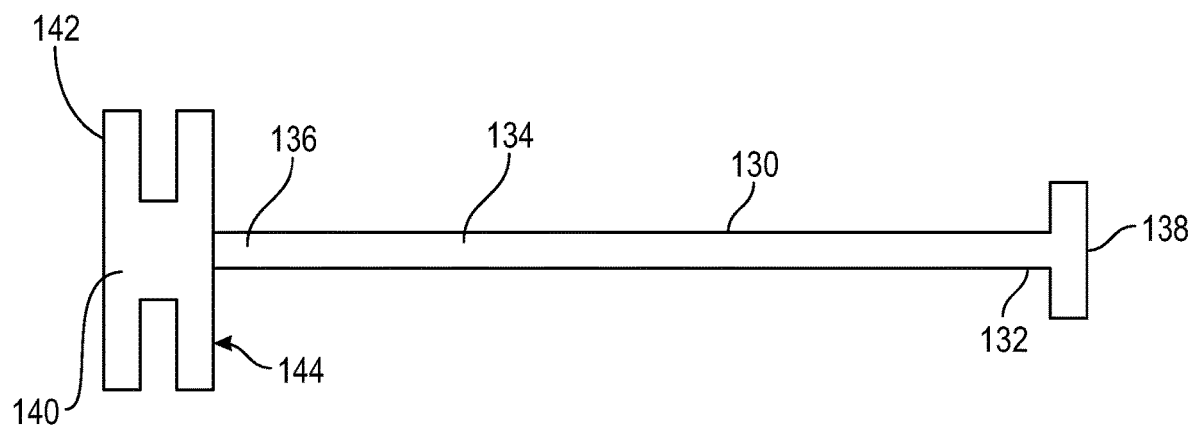
FIG. 2 shows a side view of a stopper and plunger rod of the medical device shown in FIG. 1.

FIGS. 1-2 illustrate one of more embodiments of a medical device 100 according to a first aspect of the disclosure. As shown in FIGS. 1-2, medical device 100 includes a syringe barrel 110 having an open proximal end 112 and a distal end 114 and a distal wall 116. A sidewall 118 extends from the distal end 114 to the open proximal end 112 and includes an interior surface 120 that defines a chamber 122 for retaining or holding fluids, which may include liquid medication and/or other liquids. A tip 124 extending distally from the distal wall 116. The tip 124 having an open passageway 126 therethrough in fluid communication with the chamber 122. The syringe barrel 110 may include a finger flange 128 at the open proximal end 112 extending radially outwardly from the sidewall 118. A needle hub may be utilized to attach a needle cannula to the tip 124. A needle hub may include a needle cannula with a lumen or opening therethrough and may be attached to the tip 124 so that the lumen is in fluid communication with the open passageway 126 and the chamber 122. The needle hub may include a distal end and a proximal end and a body defining a hollow space. When assembled, the tip 124 is inserted into the hollow space through the open proximal end of the needle hub until the body frictionally engages the tip 124. Alternatively, the needle cannula may be attached to the tip 124, without the use of a needle hub, using other methods known in the art. The interior surface 120 of the syringe barrel 110 may have a smooth surface that is free of any protrusions or depressions. In use, a plunger rod 130 and a stopper 140 are inserted into the open proximal end 112 of the syringe barrel 110.

As more clearly shown in FIG. 2, the plunger rod 130 has a proximal end 132, a distal end 136 and a body 134 extending from the proximal end 132 to the distal end 136. The plunger rod 130 is disposed within the chamber 122 and moveable in the proximal and distal direction within the chamber 122. The plunger rod 130 may be made of a rigid plastic or other material. Examples of such materials include polypropylene, polyethylene, polycarbonate and combinations thereof. The proximal end 132 of the plunger rod 130 includes a thumbpress 138. The distal end 136 of the plunger rod 130 includes a stopper-engaging portion. In accordance with one or more embodiments of the present invention, the stopper-engaging portion is shaped to fit within the stopper cavity of the stopper 140 and to retain the stopper 140 at the distal end 136 of the plunger rod. In a specific embodiment, the plunger rod 130 and stopper 140 may be integrally formed or permanently attached.

As more clearly shown in FIG. 2, stopper 140 having a distal end 142 and a proximal end 144. The stopper 140 includes an outside surface and an inside surface defining a stopper cavity. The stopper 140 may be formed from an elastomeric material, polymeric material or other material known in the art.

As more clearly shown in FIGS. 1-2, the medical device 100 includes a plunger rod 130 attached to a stopper 140. The stopper 140 is disposed within the chamber 122 and moveable in the proximal and distal direction within the chamber 122.

Sidewall 118 of the syringe barrel 110 includes a first sidewall portion 118A and a second sidewall portion 118B. First sidewall portion 118A is disposed at the distal end 114 of the barrel 110. First sidewall portion 118A has an inner diameter equal to or smaller than an outer diameter of the stopper 140 to form a releasable fluid-tight seal between the stopper 140 and the interior surface 120 of the sidewall 118 of the barrel 110. Second sidewall portion 118B is disposed at the open proximal end 112 of the barrel 110. Second sidewall portion 118B includes a taper defining an air purge zone 119. Second sidewall portion 118B has an inner diameter larger than the outer diameter of the stopper 140 forming a gap 150 between the interior surface 120 of the sidewall 118 and stopper 140 causing the releasable seal between the stopper 140 and the sidewall 118 of the barrel 110 to break thereby permitting air to vent from the chamber 122 while preventing liquid from exiting the chamber 122. In one or more embodiments, the inner diameter of the second sidewall portion 118B increases gradually in the proximal direction to the open proximal end 112. The inner diameter of the barrel 110 increases gradually in the proximal direction such that the gap 150 exists between the barrel 110 and stopper 140 when the stopper 140 is pulled into this location. When the device 100 is held in a tip 124 up position, the gravity force on the liquid within the chamber 122 will push the trapped air outside quickly and easily.

Formation of a seal between the stopper 140 and the first sidewall portion 118A of the barrel 110 ensures a vacuum is created between the distal face of the stopper 140 and the chamber 122 of the syringe barrel 110 so that liquid may be aspirated into the chamber 122. The structure of the stopper 140 and the sidewall 118 of the barrel prevents the seal from being released during aspiration and when the liquid is being expelled from the chamber 122 of the syringe barrel 110 but permits the release of the seal when the stopper 140 reaches the proximal end of the barrel after the desired amount of liquid is drawn and the stopper reaches the tapered portion of the second sidewall portion 118B of the syringe barrel 110 so the air within the barrel chamber 122 may be vented.

In one or more embodiments, the distal end of the plunger rod is disposed within the barrel and the stopper forms a releasable seal with the sidewall of the barrel having an inner diameter equal to or smaller than the outer diameter of the stopper. The releasable fluid-tight seal between the stopper 140 and the interior surface 120 of the sidewall 118 of the barrel 110 is broken when the stopper 140 reaches the taper of the second sidewall portion 118B at the open proximal end 112 of the barrel 110.

In one or more embodiments, upon movement of the plunger rod 130 in a distal direction relative to the taper of the second sidewall portion 118B at the open proximal end 112 of the barrel 110, the releasable seal is re-formed allowing the fluid within the chamber 122 to be expelled through the open passageway 126 of the tip 124 in fluid communication with said chamber 122.

In one or more embodiments, medical device 100 includes a barrel graduation line 160. In one or more embodiments, the second sidewall portion 118B is proximal to the barrel graduation line.

Another aspect of the present disclosure pertains to a method for filling a syringe barrel 110 with a liquid, comprising providing a medical device 100 as described herein; submerging the tip 124 of the syringe barrel 110 in a liquid; drawing an air source 170 and the liquid into the chamber 122; and evacuating the air source 170 from the chamber 122 by moving the plunger rod 130 in a proximal direction to allow the stopper 140 to break the releasable fluid-tight seal between the stopper 140 and the interior surface 120 of the sidewall 118 of the barrel 110 when the stopper 140 reaches the taper of the second sidewall portion 118B at the open proximal end 112 of the barrel 110. The force of gravity of the liquid acting upon the air source 170 trapped in the chamber 122 is the driving force for evacuating the air source 170 from the chamber 122.

Figure 3:
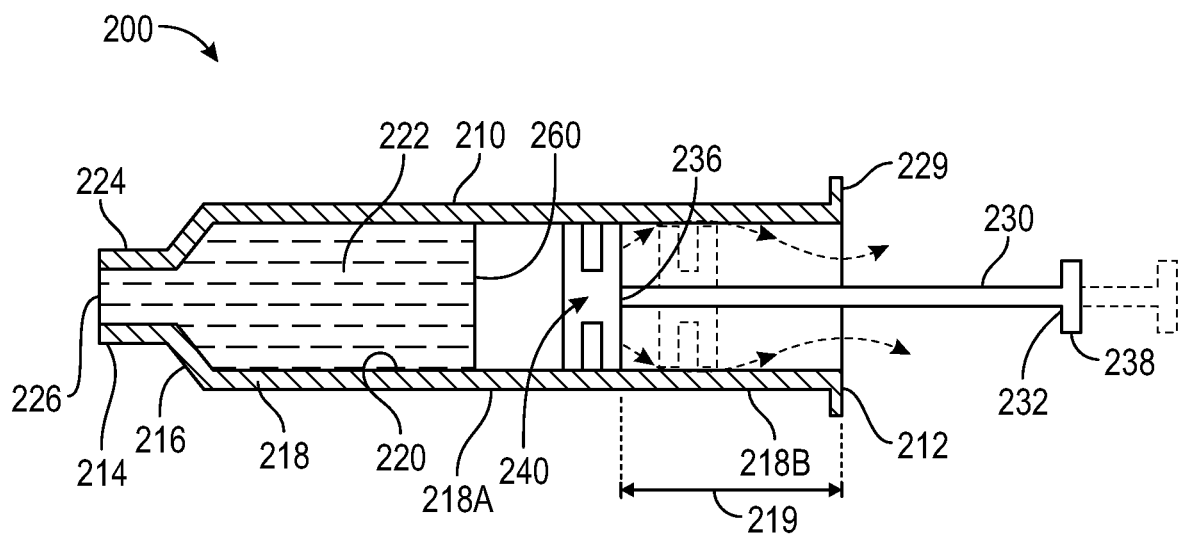
FIG. 3 shows a cross-sectional side view of a medical device having a barrel, a plunger rod and stopper according to a second aspect of the present disclosure.
Figure 4:
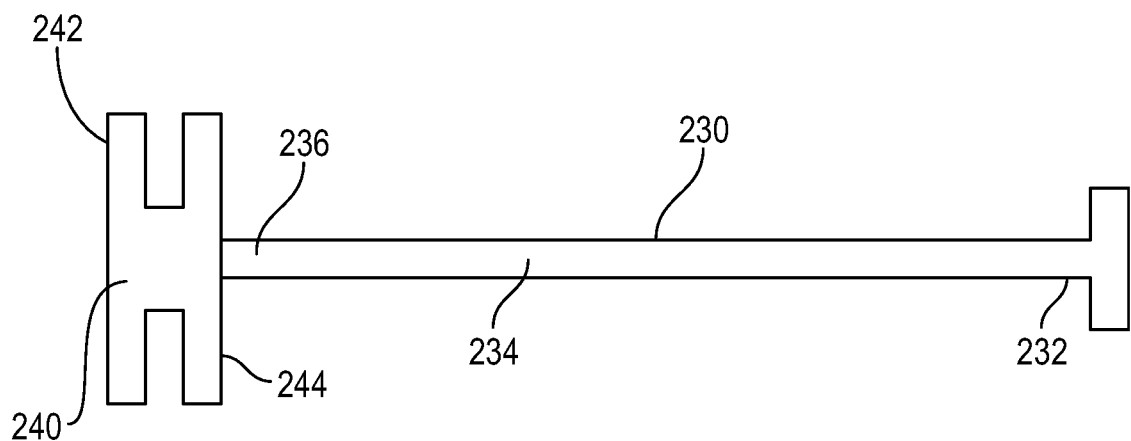
FIG. 4 shows a side view of a stopper and plunger rod of the medical device shown in FIG. 3.

FIGS. 3-5 illustrate one of more embodiments of a medical device 200 according to another aspect of the disclosure. As shown more clearly in FIG. 3, medical device 200 includes a syringe barrel 210 having an open proximal end 212 and a distal end 214 and a distal wall 216. A sidewall 218 extends from the distal end 214 to the open proximal end 212 and includes an interior surface 220 that defines a chamber 222 for retaining or holding fluids, which may include liquid medication and/or other liquids. A tip 224 extending distally from the distal wall 216. The tip 224 having an open passageway 226 therethrough in fluid communication with the chamber 222. The syringe barrel 210 may include a finger flange 229 at the open proximal end 212 extending radially outwardly from the sidewall 218. A needle hub may be utilized to attach a needle cannula to the tip 224. A needle hub may include a needle cannula with a lumen or opening therethrough and may be attached to the tip 224 so that the lumen is in fluid communication with the open passageway 226 and the chamber 222. The needle hub may include a distal end and a proximal end and a body defining a hollow space. When assembled, the tip 224 is inserted into the hollow space through the open proximal end of the needle hub until the body frictionally engages the tip 224. Alternatively, the needle cannula may be attached to the tip 224, without the use of a needle hub, using other methods known in the art. The interior surface 220 of the syringe barrel 210 may have a smooth surface that is free of any protrusions or depressions. In use, a plunger rod 230 and a stopper 240 are inserted into the open proximal end 212 of the syringe barrel 210.

As more clearly shown in FIGS. 3-4, the plunger rod 230 has a proximal end 232, a distal end 236 and a body 234 extending from the proximal end 232 to the distal end 236. The plunger rod 230 is disposed within the chamber 222 and moveable in the proximal and distal direction within the chamber 222.

As more clearly shown in FIG. 4, stopper 240 having a distal face 242 and a proximal end 244. The stopper 240 includes an outside surface and an inside surface defining a stopper cavity. The stopper 240 may be formed from an elastomeric material, polymeric material or other material known in the art.

As more clearly shown in FIGS. 3-4, the medical device 200 includes a plunger rod 230 attached to a stopper 240. The stopper 240 is disposed within the chamber 222 and moveable in the proximal and distal direction within the chamber 222.

Figure 5A:
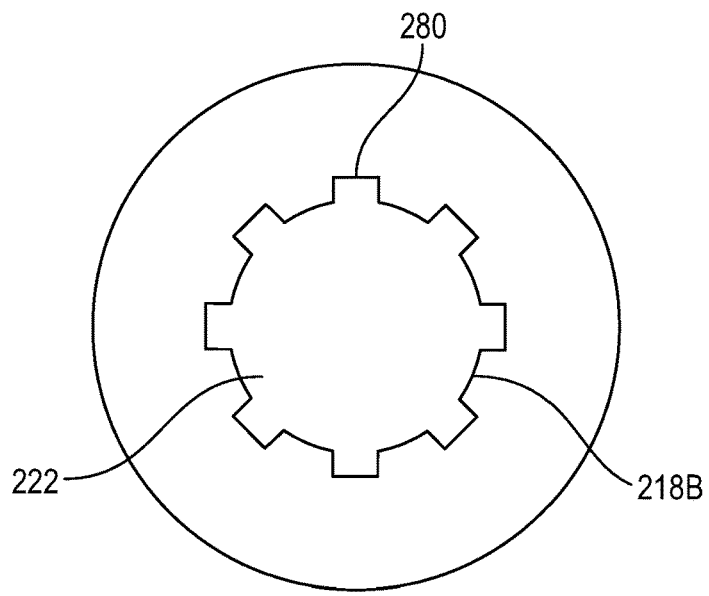
FIG. 5A shows a cross-sectional side view of a sidewall of the medical device shown in FIG. 3 having square shaped air venting grooves.
Figure 5B:
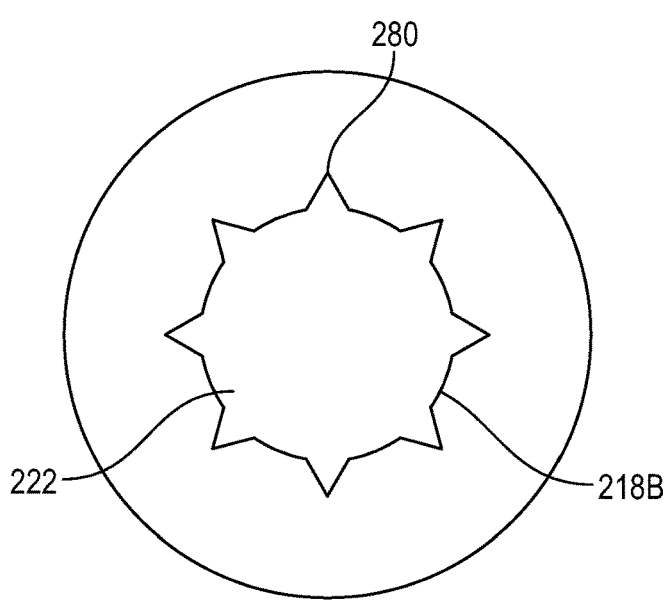
FIG. 5B shows a cross-sectional side view of a sidewall of the medical device shown in FIG. 3 having triangle shaped air venting grooves.
Figure 5C:
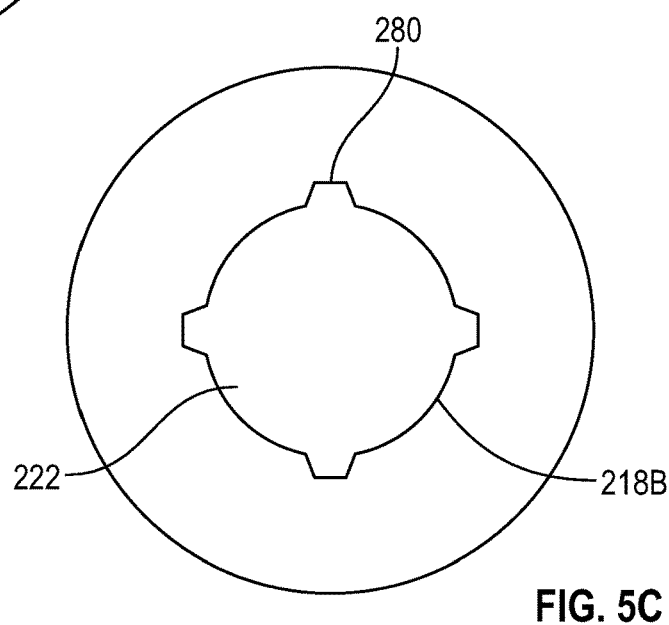
FIG. 5C shows a cross-sectional side view of a sidewall of the medical device shown in FIG. 3 having round shaped air venting grooves.

Sidewall 218 of the syringe barrel 210 includes a first sidewall portion 218A and a second sidewall portion 218B. First sidewall portion 218A is disposed at the distal end 214 of the syringe barrel 210 and forms a releasable fluid-tight seal between the stopper 240 and the interior surface 220 of the sidewall 218 of the syringe barrel 210. Second sidewall portion 218B is disposed at the open proximal end 212 of the syringe barrel 210. In one or more embodiments, the open proximal end of the barrel includes the second sidewall portion 218B having one air venting groove embedded within the second sidewall portion of the barrel to break the releasable seal between the stopper and the sidewall of the barrel for permitting air to vent from the chamber and preventing liquid from exiting the chamber. In one or more embodiments, the second sidewall portion 218B including a plurality of air venting grooves 280 embedded within the interior surface of the second sidewall portion 218B of the syringe barrel 210 to break the releasable seal between the stopper 240 and the first sidewall portion 218A of the syringe barrel 210 for permitting air to vent from the chamber 222 and preventing liquid from exiting the chamber 222. The width of the air venting groove is chosen to allow air leakage but prevent liquid to leak through. The width of the air venting groove 280 may be in the range of 0.025 mm through 1 mm. In a specific embodiment the width of the air venting groove 280 may be in the range of 0.05 mm through 0.5 mm. In one or more embodiments, the width of the air venting grooves 280 could increase gradually in the proximal direction. In one or more embodiments, plurality of air venting grooves 280 are disposed along a portion or the entire length of the inner surface of the second sidewall portion 218B of the syringe barrel 210 defining an air purge zone 219. In one or more embodiments, the plurality of air venting grooves 280 can be molded in the inner diameter of the syringe barrel 210. When the stopper 240 is over the plurality of air venting grooves 280, the air will be vented out under gravity load of the liquid in the chamber 222. The plurality of air venting grooves 280 can be sized such that the air will leak through the plurality of air venting grooves 280 while liquid will not leak out due to surface tension. In one or more embodiments, the plurality of air venting grooves 280 extends along the second sidewall portion in a direction substantially parallel to a longitudinal axis "L" of the chamber. In one or more embodiments, the plurality of air venting grooves 280 may have any desired shape, including, but not limited to, a triangular, square, rectangular, or rounded shape, as shown in FIGS. 5A-5C. In one or more embodiments, the plurality of air venting grooves 280 may be tapered. In one or more embodiments, the plurality of air venting grooves 280 may be positioned equi-distance about the circumference of the inside surface of the chamber 222. In one or more embodiments, the plurality of air venting grooves 280 may be oriented opposite from each other around a circumference of the chamber 222.

In one or more embodiments, the plurality of air venting grooves 280 may be arranged in sets of one or more individual grooves. The individual grooves comprising the plurality of air venting grooves 280 may be spaced close together from one another. In an alternate embodiment, the individual grooves comprising the plurality of air venting grooves 280 may be spaced apart from one another. In another embodiment, the plurality of air venting grooves 280 may be oriented 180° apart around a circumference of the inside surface of the cavity.

When the medical device 200 is held in a tip 224 up position, the gravity force on the liquid within the chamber 222 will push the trapped air outside quickly and easily.

In one or more embodiments, the stopper 240 forms a releasable fluid-tight seal with the first sidewall portion 218A of the syringe barrel 210 when the distal end 236 of the plunger rod 230 is disposed within the first sidewall portion 218A. The releasable fluid-tight seal between the stopper 240 and the interior surface 220 of the sidewall 218 of the syringe barrel 210 is broken when the distal end 236 of the plunger rod 230 is disposed within the second sidewall portion 218B and stopper 240 reaches the plurality of air venting grooves 280 embedded within the second sidewall portion 218B at the open proximal end 212 of the syringe barrel 210.

In one or more embodiments, upon movement of the plunger rod 230 in a distal direction from the second sidewall portion 218B towards the first sidewall portion 218A relative to the plurality of air venting grooves 280 of the second sidewall portion 218B at the open proximal end 212 of the syringe barrel 210, the releasable seal is re-formed upon contact of the stopper 240 with the first sidewall portion allowing the fluid within the chamber 222 to be expelled through the open passageway 226 of the tip 224 in fluid communication with said chamber 222.

In one or more embodiments, medical device 200 includes a barrel graduation line 260. In one or more embodiments, the second sidewall portion 218B is proximal to the barrel graduation line 260.

Another aspect of the present disclosure pertains to a method for filling a syringe barrel 210 with a liquid, comprising providing a medical device 200 as described herein; submerging the tip 224 of the syringe barrel 210 in a liquid; drawing an air source 270 and the liquid into the chamber 222 prior to reaching the plurality of air venting grooves 280 embedded within the second sidewall portion 218B; and evacuating the air source 270 from the chamber 222 by moving the plunger rod 230 in a proximal direction past the plurality of air venting grooves 280 embedded within the second sidewall portion 218B of the syringe barrel 210 to allow the stopper 240 to break the releasable fluid-tight seal between the stopper 240 and the interior surface 220 of the first sidewall portion 218A of the syringe barrel 210 when the stopper 240 reaches the plurality of air venting grooves 280 of the second sidewall portion 218B at the open proximal end 212 of the syringe barrel 210 for permitting air to vent from the chamber 222 and preventing liquid from exiting the chamber 222; and re-forming the releasable fluid-tight seal upon contact of the stopper 240 with the first sidewall portion 218A allowing the fluid within the chamber 222 to be expelled through the open passageway 226 of the tip 224 in fluid communication with said chamber 222. The force of gravity of the liquid acting upon the air source 270 trapped in the chamber 222 is the driving force for evacuating the air source 270 from the chamber 222.

FIGS. 6-9C illustrate one of more embodiments of a medical device 300 according to another aspect of the disclosure. As shown more clearly in FIGS. 6-7, medical device 300 includes a syringe barrel 310 having an open proximal end 312 and a distal end 314 and a distal wall 316. A sidewall 318 extends from the distal end 314 to the open proximal end 312 and includes an interior surface 320 that defines a chamber 322 for retaining or holding fluids, which may include liquid medication and/or other liquids. A tip 324 extending distally from the distal wall 316. The tip 324 having an open passageway 326 therethrough in fluid communication with the chamber 322. The syringe barrel 310 may include a finger flange 328 at the open proximal end 312 extending radially outwardly from the sidewall 318. A needle hub may be utilized to attach a needle cannula to the tip 324. A needle hub may include a needle cannula with a lumen or opening therethrough and may be attached to the tip 324 so that the lumen is in fluid communication with the open passageway 326 and the chamber 322. The needle hub may include a distal end and a proximal end and a body defining a hollow space. When assembled, the tip 324 is inserted into the hollow space through the open proximal end of the needle hub until the body frictionally engages the tip 324. Alternatively, the needle cannula may be attached to the tip 324, without the use of a needle hub, using other methods known in the art. The interior surface 320 of the syringe barrel 310 may have a smooth surface that is free of any protrusions or depressions. In use, a plunger rod 330 and a stopper 340 are inserted into the open proximal end 312 of the syringe barrel 310.

Figure 6:
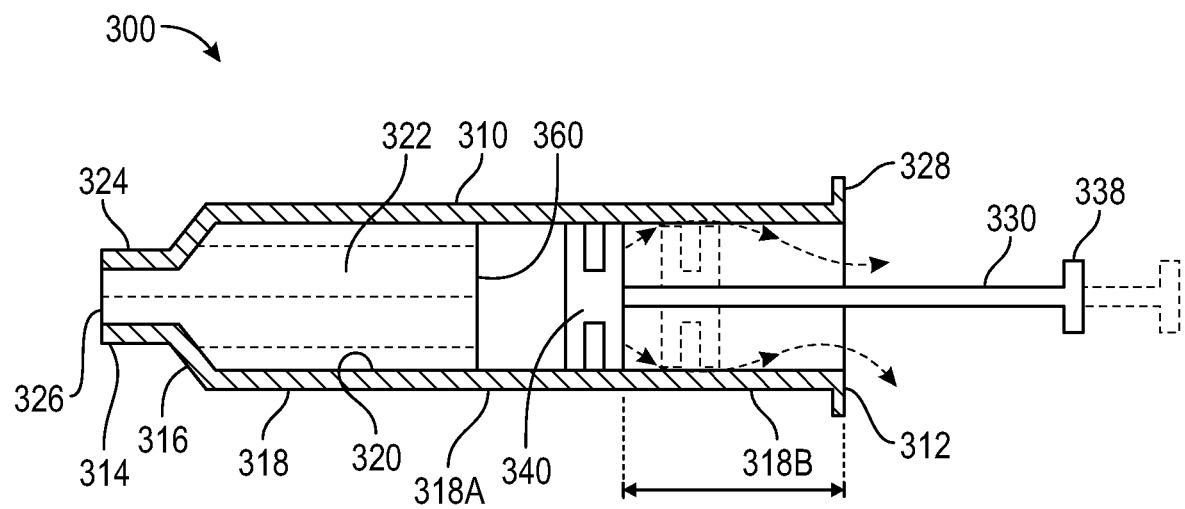
FIG. 6 shows a cross-sectional side view of a medical device having a barrel, a plunger rod and stopper according to a third aspect of the present disclosure.
Figure 7:
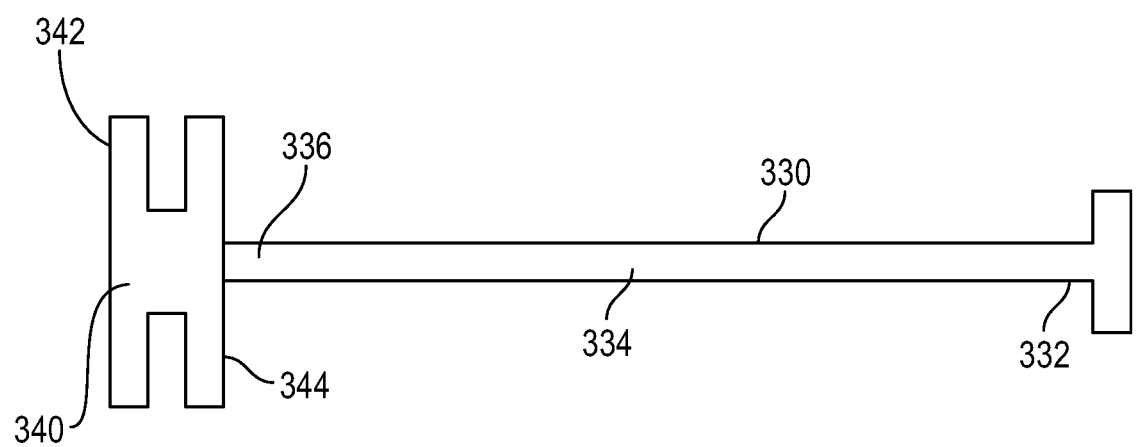
FIG. 7 shows a side view of a stopper and plunger rod of the medical device shown in FIG. 6.
Figure 8A:
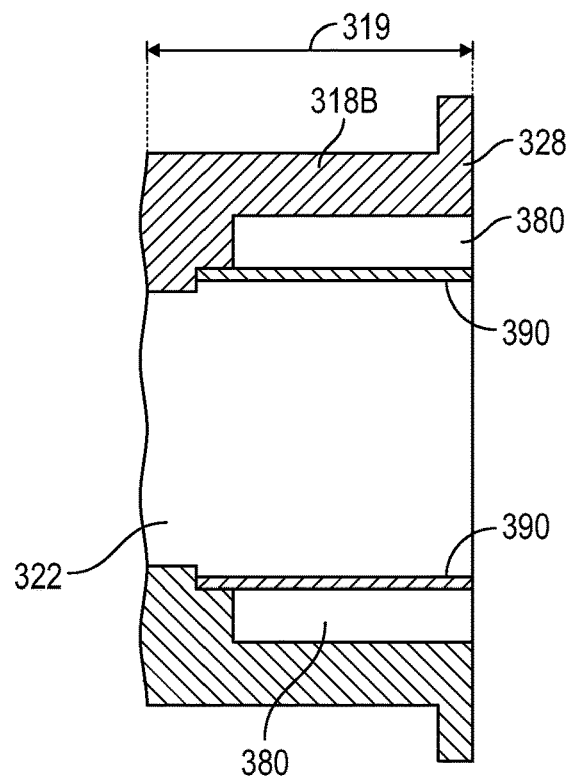
FIG. 8A shows a cross-sectional side view of a medical device shown in FIG. 6 having air venting grooves with overlain hydrophobic porous membrane air filter.
Figure 8B:
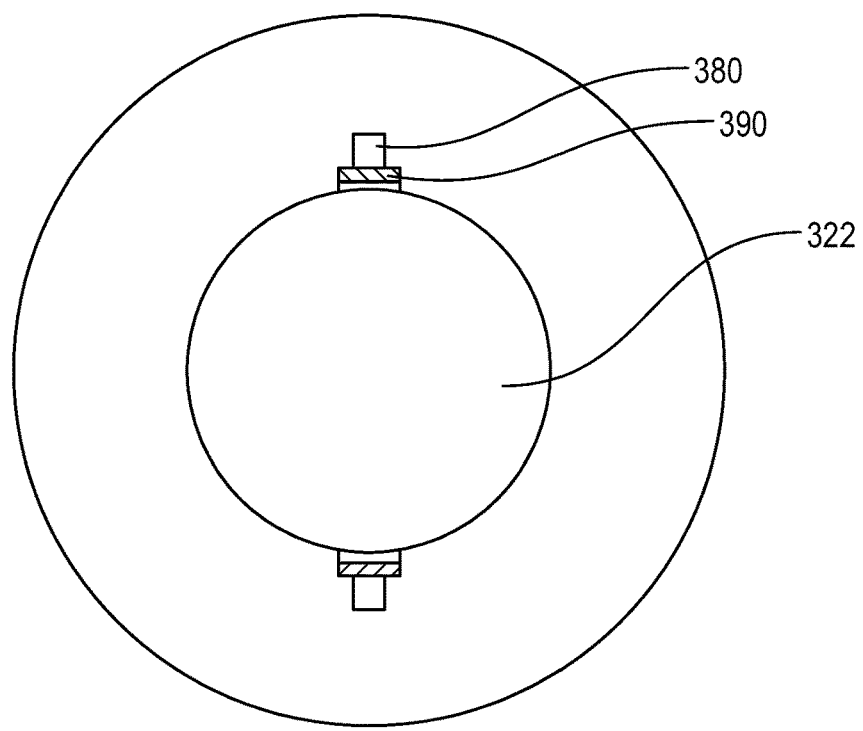
FIG. 8B shows a cross-sectional side view of a sidewall of the medical device shown in FIG. 6 having air venting grooves with overlain hydrophobic porous membrane air filter.

As more clearly shown in FIGS. 6-7, the plunger rod 330 has a proximal end 332, a distal end 336 and a body 334 extending from the proximal end 332 to the distal end 336. The plunger rod 330 is disposed within the chamber 322 and moveable in the proximal and distal direction within the chamber 322.

As more clearly shown in FIG. 7, stopper 340 having a distal face 342 and a proximal end 344. The stopper 340 includes an outside surface and an inside surface defining a stopper cavity. The stopper 340 may be formed from an elastomeric material, polymeric material or other material known in the art.

As more clearly shown in FIGS. 6-7, the medical device 300 includes a plunger rod 330 attached to a stopper 340. The stopper 340 is disposed within the chamber 322 and moveable in the proximal and distal direction within the chamber 322.

As more clearly shown in FIGS. 6-8B, sidewall 318 of the syringe barrel 310 includes a first sidewall portion 318A and a second sidewall portion 318B. First sidewall portion 318A is disposed at the distal end 314 of the syringe barrel 310 and forms a releasable fluid-tight seal between the stopper 340 and the interior surface 320 of the sidewall 318 of the syringe barrel 310. Second sidewall portion 318B is disposed at the open proximal end 312 of the barrel 310. In one or more embodiments, the open proximal end of the barrel includes the second sidewall portion 318B having one air venting groove 380 embedded within the second sidewall portion of the barrel to break the releasable seal between the stopper and the sidewall of the barrel for permitting air to vent from the chamber and preventing liquid from exiting the chamber. In one or more embodiments, as more clearly shown in FIGS. 8A-9C, the second sidewall portion 318B including a plurality of air venting grooves 380 embedded within the interior surface of the second sidewall portion 318B of the syringe barrel 310 to break the releasable seal between the stopper 340 and the first sidewall portion 318A of the syringe barrel 310 for permitting air to vent from the chamber 322 and preventing liquid from exiting the chamber 322. The width of the air venting groove 380 may be in the range of 0.025 mm through 2.0 mm. In one or more embodiments, the width of the air venting grooves 380 could increase gradually in the proximal direction. As more clearly shown in FIGS. 8A-9C, a hydrophobic porous membrane air filter 390 overlies the plurality of air venting grooves 380 embedded within the interior surface of the second sidewall portion 318B of the syringe barrel 310 to facilitate the purging of trapped air while preventing liquid from leaking out.

Figure 9A:
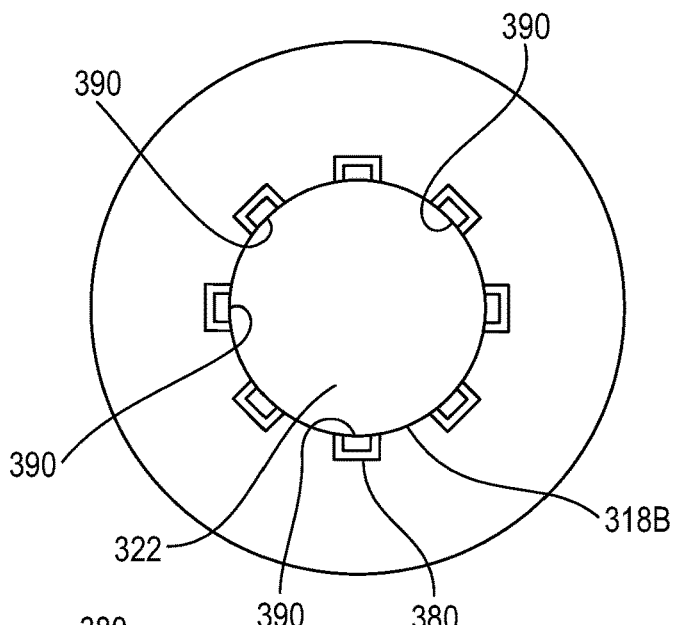
FIG. 9A shows a cross-sectional side view of a sidewall of the medical device shown in FIG. 8 having square shaped air venting grooves.
Figure 9B:
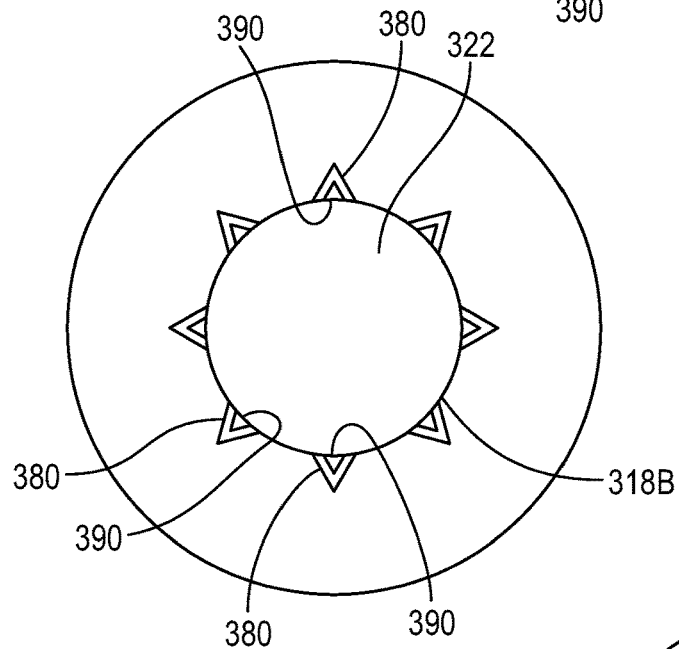
FIG. 9B shows a cross-sectional side view of a sidewall of the medical device shown in FIG. 8 having triangle shaped air venting grooves.
Figure 9C:
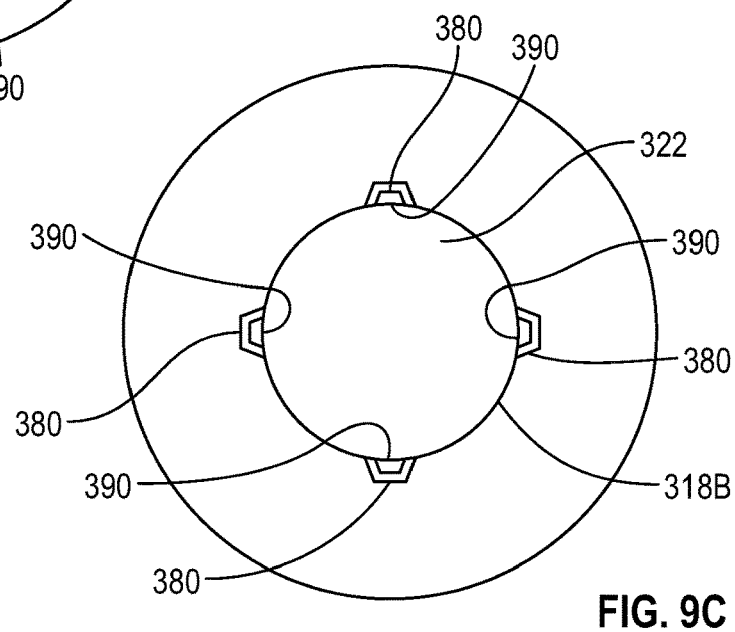
FIG. 9C shows a cross-sectional side view of a sidewall of the medical device shown in FIG. 8 having round shaped air venting grooves.

In one or more embodiments, the plurality of air venting grooves 380 with the overlain hydrophobic porous membrane air filter 390 is disposed along a portion or the entire length of the inner surface of the second sidewall portion 318B of the syringe barrel 310. In one or more embodiments, the plurality of air venting grooves 380 can be molded in the inner diameter of the syringe barrel 310. When the stopper 340 is over the plurality of air venting grooves 380 overlain with the hydrophobic porous membrane air filter 390, the air will be vented out under gravity load of the liquid in the chamber 322. The hydrophobic porous membrane air filter 390 can be sized such that the air will leak through the hydrophobic porous membrane air filter 390 while liquid will not leak out due to surface tension. The plurality of air venting grooves 380 can also be sized such that the air will leak through the plurality of air venting grooves 380 while liquid will not leak out due to surface tension. In one or more embodiments, the plurality of air venting grooves 380 overlain with the hydrophobic porous membrane air filter 390 extends along the second sidewall portion in a direction substantially parallel to a longitudinal axis "L" of the chamber. In one or more embodiments, the plurality of air venting grooves 380 may have any desired shape, including, but not limited to, a triangular, square, rectangular, or rounded shape, as shown in FIGS. 9A-9C. In one or more embodiments, the plurality of air venting grooves 380 may be tapered. In one or more embodiments, the plurality of air venting grooves 380 overlain with the hydrophobic porous membrane air filter 390 may be positioned equi-distance about the circumference of the inside surface of the chamber 322. In one or more embodiments, the plurality of air venting grooves 380 overlain with the hydrophobic porous membrane air filter 390 may be oriented opposite from each other around a circumference of the chamber 322.

In one or more embodiments, the plurality of air venting grooves 380 overlain with the hydrophobic porous membrane air filter 390 may be arranged in sets of one or more individual grooves. The individual grooves comprising the plurality of air venting grooves 380 may be spaced close together from one another. In an alternate embodiment, the individual grooves comprising the plurality of air venting grooves 380 may be spaced apart from one another. In another embodiment, the plurality of air venting grooves 380 may be oriented 180° apart around a circumference of the inside surface of the cavity.

When the medical device 300 is held in a tip 324 up position, the gravity force on the liquid within the chamber 322 will push the trapped air out of the plurality of air venting grooves 380 overlain with the hydrophobic porous membrane air filter 390 quickly and easily.

In one or more embodiments, the stopper 340 forms a releasable fluid-tight seal with the first sidewall portion 318A of the syringe barrel 310 when the distal end 236 of the plunger rod 330 is disposed within the first sidewall portion 318A. The releasable fluid-tight seal between the stopper 340 and the interior surface 320 of the sidewall 318 of the syringe barrel 310 is broken when the distal end 336 of the plunger rod 330 is disposed within the second sidewall portion 318B and stopper 340 reaches the hydrophobic porous membrane air filter 390 overlying the plurality of air venting grooves 380 embedded within the second sidewall portion 318B at the open proximal end 312 of the syringe barrel 310.

In one or more embodiments, upon movement of the plunger rod 330 in a distal direction from the second sidewall portion 318B towards the first sidewall portion 318A relative to the hydrophobic porous membrane air filter 390 overlying the plurality of air venting grooves 380 of the second sidewall portion 318B at the open proximal end 212 of the syringe barrel 310, the releasable seal is re-formed upon contact of the stopper 340 with the first sidewall portion allowing the fluid within the chamber 322 to be expelled through the open passageway 326 of the tip 324 in fluid communication with said chamber 322.

In one or more embodiments, medical device 300 includes a barrel graduation line 360. In one or more embodiments, the hydrophobic porous membrane air filter 390 overlying second sidewall portion 318B is proximal to the barrel graduation line 360.

Another aspect of the present disclosure pertains to a method for filling a syringe barrel 310 with a liquid, comprising providing a medical device 300 as described herein. The tip 324 of the syringe barrel 310 is submerged in a liquid. An air source 370 and the liquid is drawn into the chamber 322 prior to reaching the hydrophobic porous membrane air filter 390 overlying the plurality of air venting grooves 380 embedded within the second sidewall portion 318B of the syringe barrel 310. The air source 370 is evacuated from the chamber 322 by moving the plunger rod 330 in a proximal direction over the hydrophobic porous membrane air filter 390 overlying the plurality of air venting grooves 380 embedded within the second sidewall portion 318B of the syringe barrel 310 to allow the stopper 340 to break the releasable fluid-tight seal between the stopper 340 and the interior surface 320 of the first sidewall portion 318A of the syringe barrel 310 when the stopper 340 reaches the hydrophobic porous membrane air filter 390 overlying the plurality of air venting grooves 380 of the second sidewall portion 318B at the open proximal end 312 of the syringe barrel 310 for permitting air to vent from the chamber 322 and preventing liquid from exiting the chamber 322. The force of gravity of the liquid acting upon the air source 370 trapped in the chamber 322 is the driving force for evacuating the air source 370 from the chamber 322.

The releasable fluid-tight seal is re-formed upon contact of the stopper 340 with the first sidewall portion 318A allowing the fluid within the chamber 322 to be expelled through the open passageway 326 of the tip 324 in fluid communication with said chamber 322.

FIGS. 10-13 illustrate one of more alternate embodiments of a medical device 400 according to another aspect of the disclosure wherein a hydrophobic porous membrane air filter can be built into the stopper such that the air can be vented out of the trapped space but not the fluid inside. The advantage of this approach is that the stopper does not need to be pulled back to an air purge zone, thereby resulting in a more efficient dose preparation.

Figure 10:
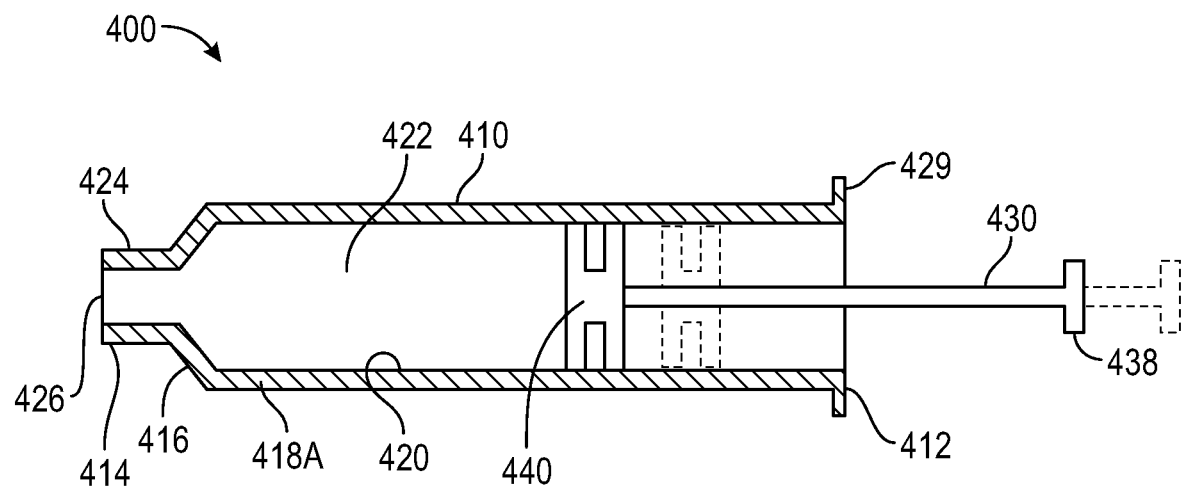
FIG. 10 shows a cross-sectional side view of a medical device having a barrel, a plunger rod and stopper according to a fourth aspect of the present disclosure.

As shown more clearly in FIG. 10, medical device 400 includes a syringe barrel 410 having an open proximal end 412 and a distal end 414 and a distal wall 416. A side-wall 418 extends from the distal end 414 to the open proximal end 412 and includes an interior surface 420 that defines a chamber 422 for retaining or holding fluids, which may include liquid medication and/or other liquids. A tip 424 extending distally from the distal wall 416. The tip 424 having an open passageway 426 therethrough in fluid communication with the chamber 422. The syringe barrel 410 may include a finger flange 429 at the open proximal end 412 extending radially outwardly from the sidewall 418. A needle hub may be utilized to attach a needle cannula to the tip 424. A needle hub may include a needle cannula with a lumen or opening therethrough and may be attached to the tip 424 so that the lumen is in fluid communication with the open passageway 426 and the chamber 422. The needle hub may include a distal end and a proximal end and a body defining a hollow space. When assembled, the tip 424 is inserted into the hollow space through the open proximal end of the needle hub until the body frictionally engages the tip 424. Alternatively, the needle cannula may be attached to the tip 424, without the use of a needle hub, using other methods known in the art. The interior surface 420 of the syringe barrel 410 may have a smooth surface that is free of any protrusions or depressions. In use, a plunger rod 430 and a stopper 440 are inserted into the open proximal end 412 of the syringe barrel 410.

Figure 11:
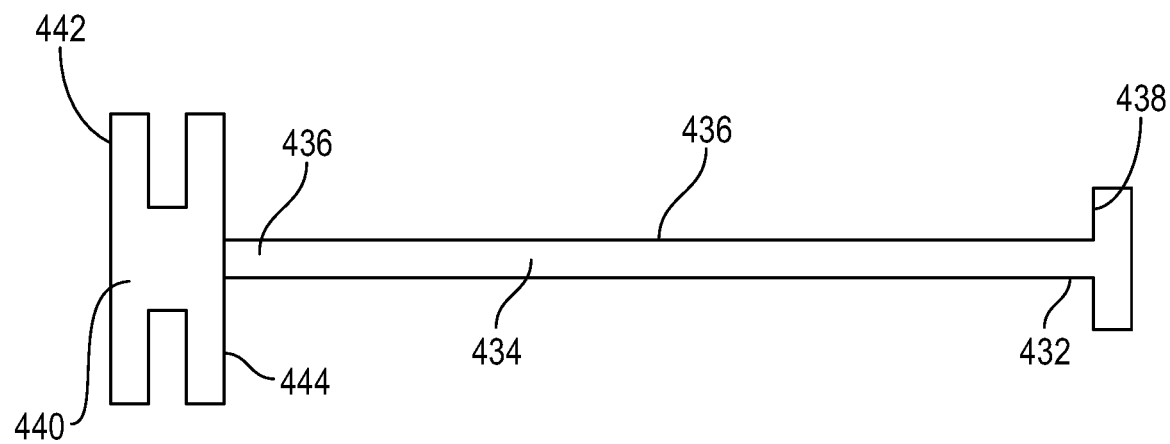
FIG. 11 shows a side view of a stopper and plunger rod of the medical device shown in FIG. 10.

As more clearly shown in FIGS. 10-11, the plunger rod 430 has a proximal end 432, a distal end 436 and a body 434 extending from the proximal end 432 to the distal end 436. The plunger rod 430 is disposed within the chamber 422 and moveable in the proximal and distal direction within the chamber 422. As more clearly shown in FIG. 10, the medical device 400 includes a plunger rod 430 attached to a stopper 440. The stopper 440 is disposed within the chamber 422 and moveable in the proximal and distal direction within the chamber 422.

Figure 12:
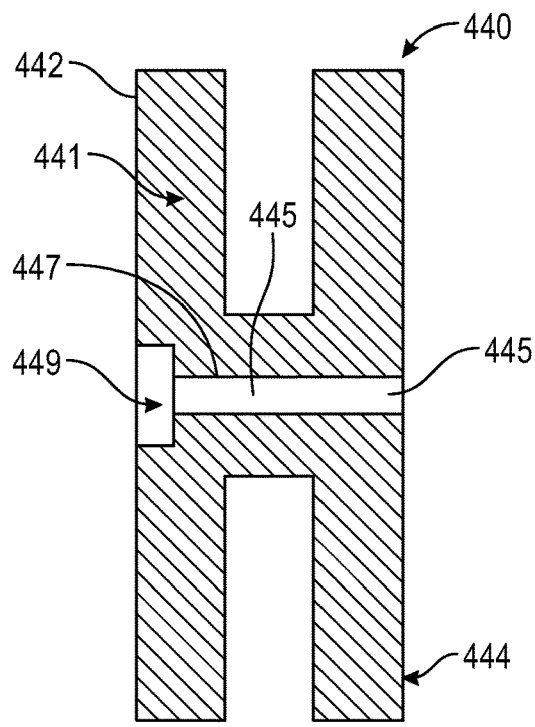
FIG. 12 shows a cross-sectional side view of a stopper of the medical device shown in FIGS. 10 and 11.

As more clearly shown in FIG. 12, stopper 440 having a distal end 441 having a distal face 442 and a proximal end 444. The stopper 440 is disposed within the chamber 422 and is moveable in the proximal and distal direction within the chamber 422, the stopper 440 forming a fluid-tight seal with the interior surface of the syringe barrel 410. The stopper 440 includes an outside surface and an interior surface defining a channel 445 within the body extending from the distal end 441 to the proximal end 444 for venting air. The distal face 442 has an opening 447 in fluid communication with channel 445. The channel 445 within the stopper has a depth, shape or cross-sectional width that allows the air within the barrel to escape through the channel 445. A porous plug 449 disposed within the channel 445 of the stopper 440 to permit air to flow from the chamber 422 and to prevent liquid from exiting the chamber 422.

The porous plug 449 of the embodiments of the medical devices described herein may include a selective barrier that defines a liquid penetration pressure and an air penetration pressure that is less than the liquid penetration pressure. In one or more embodiments, the porous plug 449 may include a hydrophilic filter, a hydrophobic filter, a swellable polymer and/or other suitable materials that are air permeable and liquid impermeable and/or combinations thereof. Examples of suitable hydrophilic filters include hydrophilic polytetrafluoroethylene membrane filters. Such filters are available from the W. L. Gore & Associates of Elkton, Md. Examples of suitable hydrophobic filters include a material known under the trademark "Tyvek" produced by E. I. duPont de Nemours and Company, Inc. of Wilmington, Delaware which is a spunbonded olefin or a material known under the trademark "Acropor" that is made of acrylonitrile polyvinyl chloride reinforced with nylon and may be obtained from Gelman Instrument Company or Ann Arbor, Mich. Other suitable hydrophobic filters include filters made of polytetrafluoroethylene, nylon, cellulose nitrate, cellulose acetate, and polethersulfone.

Suitable hydrophobic filters resist liquid from wicking through the filter at a reasonable pressure gradient. In one or more embodiments, the hydrophobic filter has a water penetration pressure, or the pressure at which water permeates or penetrates the hydrophobic filter that is greater than the air penetration pressure, or the pressure at which air permeates or penetrates the hydrophobic filter. In a specific embodiment, the water penetration pressure of the hydrophobic filter is greater than a vacuum pressure generated within the chamber of the syringe barrel or other containers and/or within the stopper and plunger rod assemblies described herein. This difference in pressure creates a pressure differential across the porous portion that drives air and liquid toward the porous portion, with the liquid impermeable property of the porous portion preventing liquid from permeating through the porous portion and allowing air to permeate through the porous portion.

The porous plug 449 may be shaped and positioned to occupy a portion of the distal face of the stopper to provide an evacuation system for the air within the syringe barrel to escape without interfering with the ability of the stopper or plunger rod to form a seal with the syringe barrel. In one or more embodiments, the porous plug 449 may be shaped and positioned to occupy the opening of the distal face 442 and is in fluid communication with channel 445 of the stopper 440. In one or more embodiments, the porous plug 449 is air permeable and liquid impermeable. In one or more embodiments, the porous plug 449 comprises a selective barrier having a liquid penetration pressure and an air penetration pressure that is less than the liquid penetration pressure.

In one or more embodiments, the porous plug 449 has a circular shape. Alternatively, the porous plug 449 may have a square and/or rectangular shape. In one or more embodiments, the porous plug 449 may be integrally formed or disposed on the distal face 442, adjacent to the opening 447.

In a specific embodiment, the porous plug 449 has a cross-sectional width that is smaller than the cross-sectional width of the distal face 442. The porous portion may also be integrally formed and/or disposed adjacent to the channel 445 on the inside surface of the stopper.

The porous plug 449 may be integrally formed on the distal face 442, with the peripheral edges of the distal face 442 and the body of the stopper remaining non-porous. The porous plug 449 may also be shaped to fit within the opening 447. For example, the porous plug 449 may extend from the distal face 442 into the channel 445. The porous plug 449 may have a periphery that is molded to a portion of the distal face 442. In one or more embodiments, the porous plug 449 may be attached to the distal face 442 of the stopper by mechanical means, for example, adhesives and/or molding. In a specific embodiment, the distal face 442 may include a pocket (not shown) for holding and securing the porous plug 449 adjacent to the distal face 442 and the opening 447 such that the porous plug 449 is in fluid communication with channel 445.

In one or more embodiments, the porous plug may be associated with the stopper to permit air to flow into the stopper cavity and to prevent liquid from entering the stopper cavity.

Figure 13:
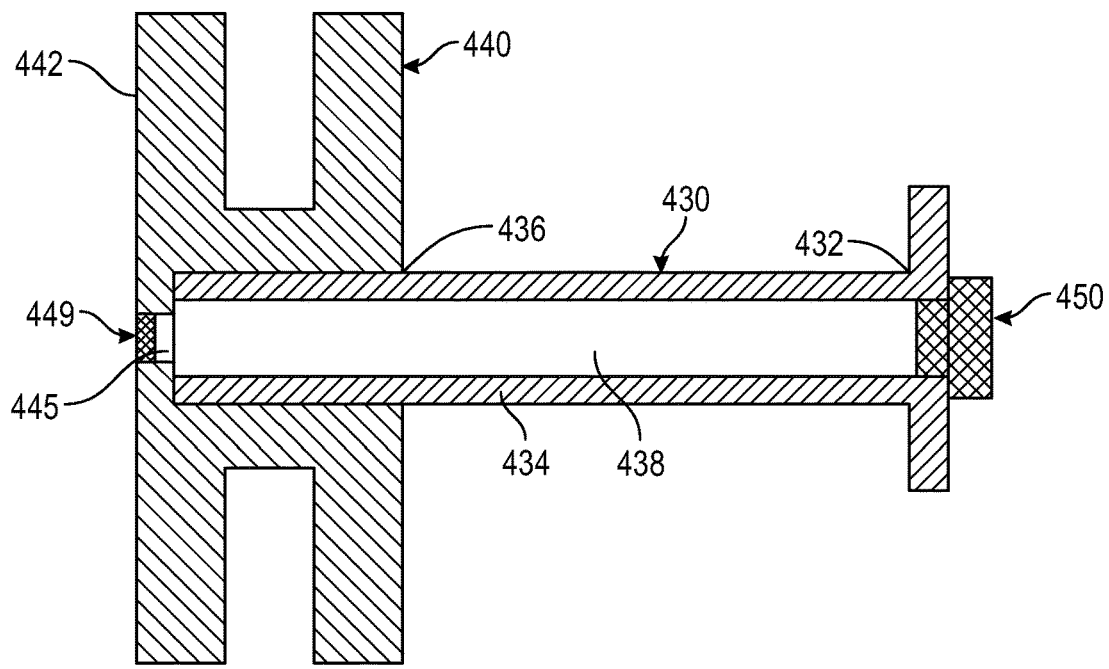
FIG. 13 shows a cross-sectional side view of an alternate embodiment of a stopper and plunger rod of the medical device shown in FIGS. 10 and 11.

In one or more embodiments, as shown in FIG. 13, plunger rod 430 has a channel 438 disposed in body 434 of the plunger rod 430 extending from the proximal end 432 to the distal end 436 that is in fluid communication with channel 445 of the stopper. A plunger cap 450 may be removably inserted in the channel 438 at the proximal end 432 of plunger rod 430. The plunger cap 450 may be shaped and positioned to occupy a portion of the channel 438 at the proximal end 432 of plunger rod 430 to provide an evacuation system for the air within the syringe barrel to escape without interfering with the ability of the stopper or plunger rod to form a seal with the syringe barrel. In one or more embodiments, the porous plug 449 may be shaped and positioned to occupy the opening of the distal face 442 and is in fluid communication with channel 445 of the stopper 440. Plunger cap 450 is inserted in a portion of the channel 438 at the proximal end 432 of plunger rod 430 during filling of the syringe an dispensing. Plunger cap 450 is removed from the channel 438 at the proximal end 432 of plunger rod 430 during venting of air from the chamber 422. In one or more embodiments, the plunger cap 450 can be designed as push button such that the air venting path in the channel 438 can be opened and closed with pushing on the plunger cap 450.

The plunger cap 450 may be formed from an elastomeric material, polymeric material or other material known in the art.

The stopper 440 may be formed from an elastomeric material, polymeric material or other material known in the art.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. A medical device comprising:
a syringe barrel including a sidewall having an interior surface defining a chamber for retaining a liquid, an open proximal end and a distal end including a distal wall with a tip extending distally therefrom having an open passageway in fluid communication with said chamber, the sidewall having a first sidewall portion and a second sidewall portion;
a plunger rod comprising a proximal end, a distal end and a body extending from the proximal end to the distal end, the plunger rod disposed within the chamber and moveable in the proximal direction and the distal direction within the chamber;
a stopper disposed within the chamber and moveable in the proximal direction and the distal direction within the chamber, the stopper including a distal face and a proximal end; and
the distal end of the barrel includes the first sidewall portion to form a releasable fluid-tight seal between the stopper and the interior surface of the first sidewall portion of the barrel, the open proximal end of the barrel includes the second sidewall portion including a plurality of air venting grooves embedded within the interior surface of the second sidewall portion of the barrel to break the releasable fluid-tight seal between the stopper and the sidewall of the barrel for permitting air to vent from the chamber and preventing liquid from exiting the chamber, and a porous membrane disposed over the plurality of air venting grooves to permit air flow out of the chamber and to prevent the liquid from exiting the chamber, the porous membrane extending in a direction substantially parallel to a longitudinal axis of the chamber.

2. The medical device of claim 1, wherein the stopper forms the releasable fluid-tight seal with the first sidewall portion of the barrel when the distal end of the plunger rod is disposed within the first sidewall portion.

3. The medical device of claim 2, wherein the stopper breaks the releasable fluid-tight seal between the stopper and the first sidewall portion of the barrel when the distal end of the plunger rod is disposed within the second sidewall portion.

4. The medical device of claim 3, wherein upon movement of the plunger rod in the distal direction from the second sidewall portion towards the first sidewall portion, the releasable fluid-tight seal is re-formed upon contact of the stopper with the first sidewall portion allowing the liquid within the chamber to be expelled through the open passageway of the tip in fluid communication with said chamber.

5. The medical device of claim 1, wherein the plurality of air venting grooves may be disposed 1-360° apart.

6. The medical device of claim 5, wherein the plurality of air venting grooves may be disposed 180° apart.

7. The medical device of claim 1, wherein the plurality of air venting grooves extends in the direction substantially parallel to the longitudinal axis of the chamber.

8. The medical device of claim 1, wherein the plurality of air venting grooves have a triangular, square, rectangular, or rounded shape.

9. The medical device of claim 8, wherein the plurality of air venting grooves have a square shape.

10. The medical device of claim 8, wherein the plurality of air venting grooves have a triangular shape.

11. The medical device of claim 8, wherein the plurality of air venting grooves have a rounded shape.

12. The medical device of claim 1, wherein the plurality of air venting grooves are disposed along a portion of the second sidewall portion.

13. The medical device of claim 1, wherein the plurality of air venting grooves are disposed along an entire length of the second sidewall portion.

14. A method for filling a medical device with liquid, comprising:
providing the medical device of claim 1;
submerging the tip of the syringe barrel in the liquid;
drawing an air source and the liquid into the chamber prior to reaching the plurality of air venting grooves embedded within the second sidewall portion of the barrel;
evacuating the air source from the chamber by moving the plunger rod in the proximal direction past the plurality of air venting grooves embedded within the second sidewall portion of the barrel to allow the stopper to break the releasable fluid-tight seal between the stopper and the interior surface of the first sidewall portion of the barrel for permitting the air to vent from the chamber and preventing the liquid from exiting the chamber; and
re-forming the releasable fluid-tight seal upon contact of the stopper with the first sidewall portion allowing the liquid within the chamber to be expelled through the open passageway of the tip in fluid communication with said chamber.

15. The medical device of claim 1, wherein each of the plurality of air venting grooves independently has a width in a range of from 0.025 mm to 2.0 mm.

16. The medical device of claim 1, wherein each of the plurality of air venting grooves independently has a width that increases gradually in the proximal direction to the open proximal end.

* * * * *